United States Patent [19]

Kameda et al.

[11] Patent Number: 4,780,421

[45] Date of Patent: Oct. 25, 1988

[54] CLEAVABLE LABELS FOR USE IN BINDING ASSAYS

[75] Inventors: Naomi Kameda, Woodside; Gerald L. Rowley, San Jose, both of Calif.

[73] Assignee: Sclavo Inc., Sunnyvale, Calif.

[21] Appl. No.: 847,505

[22] Filed: Apr. 3, 1986

[51] Int. Cl.$^4$ ................. G01N 33/543; G01N 33/536
[52] U.S. Cl. ........................................ 436/518; 435/7; 436/536; 436/537; 436/538; 436/541; 436/542; 436/545; 436/800; 436/824
[58] Field of Search ............... 436/518, 542, 545, 804, 436/536–538, 541, 800, 824; 435/7

[56] References Cited

U.S. PATENT DOCUMENTS

| | | | |
|---|---|---|---|
| 4,231,999 | 10/1980 | Carlsson et al. | 435/7 |
| 4,232,119 | 10/1980 | Carlsson et al. | 424/1 |
| 4,272,506 | 6/1981 | Schwarzberg | 435/7 |
| 4,373,932 | 2/1983 | Gribnau et al. | 436/501 |
| 4,434,236 | 2/1984 | Freytag | 436/512 |
| 4,548,908 | 10/1985 | Kameda | 436/500 |
| 4,576,912 | 3/1986 | Yaverbaum et al. | 435/7 |
| 4,652,519 | 3/1987 | Warshawsky et al. | 435/7 |

OTHER PUBLICATIONS

Smith et al., (1981) Ann. Clin. Biochem. 18:253–274.
Chromy et al., "Use of N-Methyl-D-glucamine as Buffer in the Determination of Serum Alkaline Phosphotase Activity" Clin. Chem. 27:1729–1732 (1981).
Chu et al., "Synthesis of an Amplifiable Reporter RNA for Bioassays" Nucleic Acids Res. 14:5591–5603 (Jul. 1986).

*Primary Examiner*—Christine M. Nucker
*Attorney, Agent, or Firm*—Ciotti & Murashige, Irell & Manella

[57] ABSTRACT

An improvement in an assay method which relies on the detection of a labeled, solubilized specific binding complex is achieved by linking the label to a component of the complex through a bond cleavable under conditions compatible with the assay and with the complex in solution.

14 Claims, No Drawings

CLEAVABLE LABELS FOR USE IN BINDING ASSAYS

TECHNICAL FIELD

The invention relates to immunoassay or other specific binding procedures, especially fluorescence-based procedures. Specifically, the invention relates to methods of performing assays which use solubilized specific complexes, especially immune complexes. The method permits measurement of labeling moieties in independent form, especially those labels which will result in quantitation of the fluorescence of independent fluorophores in solution.

BACKGROUND ART

The use of immunoglobulin/antigen interactions as the basis for assuring specificity in quantitative assays has now been practiced for more than two decades. The literature describing a variety of such assays is extensive, and the number of possible protocols is almost prohibitive of a list which is all inclusive. The particular methods to which this invention is directed involve formation of a labeled immune complex or other specific complex and solubilizing this complex. There are a large number of protocols for even this limited approach, which, however, have some features in common.

Of course, at least one component involved in the assay must be, or become, detectable in some manner. In this majority of cases, this means that one of the participants in the specific reaction such as an immunoreaction must be labeled in some fashion. Various labels have been employed: radioactive isotopes, fluorophores, colored substances, enzymes (which can then be used to catalyze reactions with detectable products of reactants) and even macroscopic particles which permit visualization. The most sensitive of these assays utilize enzymes, radioactive substances, or fluorophores.

In all these procedures, the quantity of label measured must be a function of the quantity of analyte present in the sample. This can be arranged, basically, in two ways: either the labeled component is caused to react directly or indirectly with the analyte in the sample, or the analyte in the sample is allowed to compete with the component carrying the label for a substance specifically reactive with the analyte.

In most protocols, a physical separation must be effected between the affinity partners which have reacted by virtue of the specific reaction and those that have not. Most frequently, the immune or other complexes formed are either precipitated or are adsorbed to a solid support. If precipitated, the complexes are generally harvested by centrifugation; if adsorbed to a solid support, the complexes are separated from nonreactive materials by washing with solutions which do not react with adsorbent. In most assay designs, the label which is used for quantitation is included in and measured in the solid phase. However, in the assays to which this invention is addressed, the specifically formed complex is redissolved before measuring the label.

One such embodiment is described in U.S. Pat. No. 4,548,908 wherein the entire precipitated immune complex containing a fluorophore is dissolved in base for reading with a fluorometer. Since the base dissolves the entire complex, and does not separate the fluorophores from the complex, the fluorophores may be close enough to each other to quench, thereby reducing the total radiation potentially detectable from more dilute fluorophores (see, e.g., Smith, D. S., et al, Ann Clin Biochem (1981) 18: 253–274). Thus, there is a limitation on the amount of detectable emitted light due to the proximity of the fluorophores to each other even on the solubilized proteins. This problem arises also for alternative forms of labeling, in that, for example, enzyme activity may be damped by the protein to which it is conjugated and (less seriously) radiation may be absorbed by the complex to which the radioisotope is bound.

It would be helpful in increasing sensitivity and accuracy if the fluorophore or other label could be individually resolubilized and detached from the protein or other affinity partner to which it is conjugated, whether or not the specific complex is itself resolubilized. Were this achievable, the fluorophore molecules or other label would behave as independent moieties so that they have increased detectability, i.e., reduced capacity to quench, or otherwise alter, their detectability.

U.S. Pat. No. 4,231,999 to Carlsson et al discloses the use of a splittable bond in the conjugation of a label to a component of an immunoassay which permits the label to be detached for measurement. The label is detached directly from the solid support, and is freed for the purpose of overcoming difficulties in measurement of label on solid materials. For fluorescent-labeled assays which involve reading emitted light where the fluorescent complex is adsorbed to a solid support, for example, the high concentration of fluorophore on the solid results in too high a level of light for accurate measurement (akin to attempting to view the stars in the daytime). To solve this problem of high emission a number of suggested splittable bonds are disclosed, including disulfide linkages. U.S. Pat. No. 3,232,119, also to Carlsson et al, specifically outlines preferred procedures for preparing labeled moieties conjugated through disulfide linkages which are cleavable through reduction. Again, the immune complex formed is directly cleaved by reduction prior to measurement of label.

The Carlsson disclosures suffer from the disadvantage that the sensitivity of the assay is limited by the availability of cleavable bonds at the surface of the immune complex. The reaction must either be conducted as a monolayer, or a loss of accuracy will result from failure to cleave the bonds of the conjugate which are internal to the bulk complex. The invention herein solves these problems by utilizing a presolubilization step prior to detachment of label.

DISCLOSURE OF THE INVENTION

The invention provides an improvement in specific binding assays, such as immunoassay procedures, utilizing labels, especially fluorophores, which permit an increase in sensitivity of these assays, as well as contributing to the ease of performing them. The assays all include formation of a specific complex, such as an immune complex, separation of the complex from the reaction mixture by, for example, precipitation or adsorption to solid support, and dissolution of the complex. Label is conjugated to the desired specifically reactive component through a bond which is readily cleavable under conditions imposed after the immunoreaction or other specific reaction and dissolution has taken place. After resolubilization, this bond is cleaved. In this manner, the amount of label carried with the immune or other specific reagent (which is reacted in a manner proportional to the amount of analyte) can be completely recovered from the entire immune or other specific reactive complex independent of its conjugation partner.

Thus, in one aspect, the invention relates to an improvement in the known method for determining the amount of an analyte in a sample suspected of containing the analyte. In one format, the traditional method comprises reacting said sample with a reagent containing at least one substance specifically reactive with said analyte, obtaining a specific complex, separating the complex from the liquid phase, and dissolving the complex to obtain it in solubilized form, wherein the solubilized complex contains a detectable label. In the traditional manner of conducting these assays, the amount of label is read directly from the complex.

The improvement of the invention comprises providing the label as a conjugate to a component of the complex, wherein the conjugate contains at least one bond cleavable under conditions compatible with the assay, and wherein the cleavable bond permits the label to be released from the solubilized complex prior to measuring the amount of said label.

The invention also relates to kits suitable for performance of the assays, and to methods of preparing these reagents. It also relates to certain labeled conjugates suitable for the method of the invention, including those of the formulas (F—NHCSNHCH$_2$CH$_2$—S)$_m$—X,

FNHCSNHCH$_2$CH$_2$SH, and (FNHCSNHCH$_2$CH$_2$S—)$_2$ wherein F is a fluorophore and X is a specific reaction participant.

MODES OF CARRYING OUT THE INVENTION

A. Definitions

As used herein, "substance specifically reactive with analyte" refers to a reagent which is capable of reacting with whatever comprises the analyte, but not with contaminants under the conditions of the assay. This reagent may most commonly be a component of an antigen/antibody reaction; it can either be the antigen or the antibody. The immunospecific reagent may be either a complete immunoglobulin or antibody specific for the antigen, or may be an "immunospecific portion thereof", such as the F(ab')$_2$ fragment, or other portion of the antibody that reads specifically with antigen. The antigen can be any of a variety of materials, including immunoglobulin or fragments thereof. It may be a protein, a carbohydrate, or any molecule of sufficient size to constitute an antigenic determinant. Antibodies, in general, can be raised against sites of approximately 10 Å or more if the materials comprising such sites are made sufficiently large to be immunogenic by conjugation to carrier molecules. This is frequently the practice in generating antibodies to, for example, smaller peptide units or other small molecules in specific vaccines.

The "substance specifically reactive with analyte" also refers to the components of reactions which are not immunoreactions, but which retain the property of specificity in the face of contaminants. For example, certain lectins react specifically with the carbohydrate moieties on certain proteins, certain receptors found on cell surfaces react specifically with their target materials; biotin reacts specifically with avidin. Thus, "substance specifically reactive with analyte" is used as a general term to indicate the other partner in an affinity reaction between an analyte substance and a reagent specifically reactive with it, including, but not limited to, antibody and a material containing an antigenic determinant for which it is specific.

More generally, a "specific reaction participant" may refer either to the above reagent reactive with analyte or to the analyte itself. Each is the counterpart of the other in the highly specific interaction which forms the basis for the assay.

"Conditions compatible with the assay" as they relate to the reactivity of the "cleavable" bonds in the conjugates of the invention, refer to conditions which do not interfere with the conduct of the assay, but which succeed in liberation of the label. Thus, the bond is sufficiently stable that it is not dissociated during the formation and solubilization of the complex formed in the specific reactions of the assay, but can be cleaved by imposing conditions which do not otherwise interfere with the complex.

Thus, "cleavable bond" refers to a bond through which a substance participating in the complexing reaction is conjugated to label. The conjugation may be either through an independent linking species, described below, or may be a direct conjugation between the component involved in the specific complexing reaction and the labeled material.

"Specifically cleavable linker" refers to a substance which is used to conjugate two separate moieties and which provides a cleavage site for separating the conjugated entities under specific predetermined conditions. For use in the invention, the specifically cleavable linker should be stable under the conditions of storage and assay and, in particular, under conditions associated with the presence of serum. Thus, the linkage should be stable to neutral pH and physiological ionic strengths and under the conditions under which immune or other complex is formed. However, it should cleave rapidly upon completion of the separation and solubilization or the complex when the cleavage-specific conditions are supplied. Such conditions include oxidizing and reducing reagents, pH conditions, specific enzyme cleavage, and other reagents which promote specific cleavage reactions.

"Fluorophore" refers to a substance or portion thereof which is capable of exhibiting fluorescence in the detectable range. Typically, this fluorescence is in the visible region, and these are common techniques for its quantitation. Examples of fluorophores which are commonly used include fluorescein, (usually supplied as fluorescein isothiocyanate [FITC] or fluorescein amine), rhodamine, dansyl, and umbelliferone.

B. General Method

The cleavable bond of the invention may be used to conjugate label either to the analyte itself, or to substances directly or indirectly specifically reactive with it. In the first instance, the labeled analyte will compete with the unlabeled analyte of the sample for a substance specifically reactive with analyte. The amount of label bound to this substance will then be inversely proportional to the concentration of the analyte in the sample. Alternatively, the substance specifically reactive with the analyte may be conjugated through the cleavable bond to the label, or the label may be conjugated to a second reactive substance reactive with the substance which reacts directly with the analyte in a sandwich-type assay. Clearly, the sandwich can be extended to many layers if desired, but, generally, such protocols involve reaction of the sample containing analyte with a first specifically reacting substance, followed by reaction with a labeled material which is reactive for this first substance. In any event, the product of the reaction sequence will be a precipitated or adsorbed complex containing label, the concentration of which label depends on the amount of analyte in the sample being analyzed. The precipitate or complex is then solubilized.

The variety of such protocols is well understood in the art. For example, where the analyte is an antigen, a common protocol is to provide labeled antigen to compete with that in the sample for an antibody specific to this antigen. The complex may be further insolubilized by the addition of a second antibody which either reacts with a different antigenic determinant on the antigen or which reacts with the antibody used in the original complexation. The resulting precipitate is then separated from the liquid phase and redissolved.

In another typical approach, rather than attaching label to the antigen in competition with the analyte, an antibody to the analyte antigen is provided with a label and is used to form the original immune complex which can then be further insolubilized by addition of another antibody. In another more common embodiment, the label is carried by this second antibody rather than the primary complexing immunoglobulin, Alternatively, if the analyte is itself an antibody, the immune complex may be formed using either an antigen specific against this antibody or an antibody raised against it. If an antigen is selected, again either a competitive antibody may be labeled, or the antigen itself may carry the label. In still another alternative, an antibody raised to one of the members of the original complex carries the label.

All of the foregoing can be modified by adsorbing or covalently attaching one of the reaction components to a solid support and obtaining a specific complex attached to this support. For example, an antibody specific to an antigen analyte can be adsorbed, treated with the sample to be analyzed, and then with another antibody reactive to the antigen. The label may be carried either by a competitor to the analyte or by the second antibody layer.

In any event, after the immune complex is formed, separated from the reaction mixture, for example, either by precipitation or by virtue of adsorption to solid support, and then resolubilized, the cleavable bond which holds the label to one of the components of the complex is exposed to conditions which result in severing this bond.

Part of the contribution of the invention lies in providing a mechanism for labeling a component of the specific complex formed in such a way that it remains stable during the complexing and washing procedures, but is disassembled on demand to yield a solubilized label free of the complex or any component thereof. This is achieved by utilizing a specific reaction participant conjugated to a label by the specifically cleavable bond.

The cleavable bond may be directly formed between the specific complexing reaction participant and the label, or may be effected using a linker.

In general, such linkers are characterized by moieties which contain:

(1) a first reaction site for "permanent" conjugation to the label;

(2) another site physically separated from the first for conjugation to the specific reaction participant; and (3) between these sites, a cleavable bond.

Other modifications are, of course, possible and include those wherein the property of (1) or (2) is missing, i.e., wherein the cleavable bond conjugates the linker to one or the other of the label or specific reaction participant.

The nature of the advantage of cleaving the label to obtain an independent moiety depends on the nature of the label. For fluorophores, the resulting free molecules are sufficiently diluted to overcome self-quenching.

Preparation of Linkers and Labeled Reagents

For binding to the label, a variety of functionalities is appropriate, including amino groups, thiol groups, and active esters. For binding to the specific complex participant, a variety is also available, especially as this substance may be of a variety of compositions. If, as is most commonly the case, the participant in the complexation is a protein, a functionality capable of the generation of disulfide, thioether, or amide linkages may conveniently be used.

The specifically cleavable bond itself may include a disulfide linkage (cleavable by, for example, dithioerythritol) dihydroxy moiety (cleavable by periodate), or a series of amino acid residues which offer a specific cleavage site for proteases.

Certain commercially available linkers may be suitable. For example, BSOCOES (Pierce Chemical Co.) is a homolinker capable of forming amide linkages with two different amino group-containing materials, and has a base cleavable site. DST is similarly a homolinker capable of forming amide linkages, and is cleavable by periodate. EGS contains similar linking functionality but is cleavable by hydroxylamine. DSP is a homolinker capable of forming amide linkages, but is cleavable by thiol.

Alternatively, the specific disulfide reagents and intermediates are prepared as described in the examples below.

The following examples are intended to illustrate but not to limit the invention.

EXAMPLE 1

Preparation of
1,6-Di-(5-fluoroesceinylthioureido)-3,4-dithiahexane;
(DFDTH)

$((F-NHCSNHCH_2CH_2S-)_2)$

To a round bottom flask containing 10 ml of a solvent mixture of pyridine, water and triethylamine (9:1.5:0.1 V/v/v) was dissolved 90 mg (0.4 mmoles) of cystamine dihydrochloride. Fluorescein isothiocyanate (FITC, 0.8 mmoles, 325 mg) was added to the above solution in portions during a period of 30 minutes. The reaction mixture was allowed to stir at ambient temperature overnight. Removal of the solvents under reduced pressure gave an orange solid. This material was slurried in 10 ml of $H_2O$ and 25 ml of 0.2M of ammonium acetate, then washed with 12 ml of water. Further purification was done by dissolution in 2 ml of 1N NaOH and precipitation with 6N HCl. The precipitation procedure was repeated three more times. The crude product title compound was 190 mg after drying ($P_2O_5$, 60° C.). An analytical sample was obtained by preparative TLC on silica with chloroform:methanol:concentrated ammonium hydroxide (v/v/v, 10:10:3), the plate was dried, and then redeveloped with ethyl acetate:methanol:5N ammonium hydroxide (v/v/v, 6:3:1).

Microanalysis=Calc. for $C_{46}H_{35}N_4O_{10}S_4$=C, 59.35; H, 3.66; N, 6.02; O, 17.20; S, 13.76.

Found: C, 56.28; H, 3.97; N, 5.53; S, 12.66; ash, 5.29. Corrected for ash: C, 59.24; H, 4.18; N, 5.82; S, 13.33.

EXAMPLE 2

Preparation of 3-(2-Pyridyl dithio)-propionyl—F(ab')$_2$ Conjugates; (PDTP$_n$—F(ab')$_2$ ((Py—S—S—$CH_2CH_2CO$)$_n$—F(ab')$_2$)

Freeze dried rabbit F(ab')$_2$ (3.0 mg, Jackson Immunoresearch Labs) was dissolved in 0.5 ml of 0.10M tris, 5 mM ethylenediamine tetraacetic disodium salt (EDTA), pH 8.0. The extract protein concentration was determined at 280 mm using extinction of 1.48 $g^{-1}$ 1 $cm^{-1}$ and molecular weight of F(ab')$_2$ of 92,000. N-Succinimidyl-3-(2 pyridyl dithio)-propionate (SPDP) (3.1 mg, Pierce) was dissolved in 100 μl dry dimethylformamide and stored under argon. SPDP solution, 6 μl, was added in 0.5 μl increments, one addition per 15 seconds to rapidly stirring F(ab')$_2$ solution at 4° C. The mixture was stirred for one hour after last addition, then was dialyzed against 5–125 ml portions of 0.1M phosphate, 5 mM EDTA, pH 6.0, over two days at 4° C. The product was analyzed for incorporation of PDTP groups of the protein by addition of 1 μl cysteamine hydrochloride (1.3×10$^{-2}$M, Sigma) to 24 μl of SPDP-labeled F(ab')$_2$, 76 μl of 0.1M phosphate-5 mM EDTA-pH 6.0 buffer, and 200 μl of 0.05 M tris pH 8.0 buffer. The number of 2-thiopyridine groups liberated from the protein was determined at 343 nm using an extinction of 7,600M$^{-1}$cm$^{-1}$ and using the original protein concentration corrected for dilution. The product has 12 bound PDTP groups per mole. In an identical manner, a second conjugate was prepared using 2 μl of the above SPDP in dry DMF solution to label F(ab)$_2$ to give the product of 6 PDTP groups per mole.

In a similar manner, conjugates of other specific reaction participants, including ferritin, IgE, goat anti-IgE, and Triiodothyronine (T$_3$) are prepared.

EXAMPLE 3

Preparation of Cleavable Labeled Reagent: 7-(5-fluoresceinylthioureido)-4,5-dithiaheptanoyl-F(ab')$_2$Conjugates; F'$_m$F(ab')$_2$ ((F-NHCSNHCH$_2$CH$_2$—S—S—CH$_2$CH$_2$CO)$_m$—F-(ab')2)

The DFDTH prepared in Example 1 was reduced to the sulfhydryl monomer, F-NHCSNHCH$_2$CH$_2$SH, by dissolving 2.0 mg of DFDTH in 80 μl DMF, 50 μl deionized water, and 10μ of 0.5M sodium carbonate, pH 9.5, with warming to 50° C. The resulting solution was slowly added to 1860 μl of 0.1M phosphate, 5 mM EDTA, pH 6.0 buffer with stirring. The sulfhydryl monomer stock, solution 100 μl, was mixed with 100 μl of 0.5M tris pH 8.8 and 18 μl of 10 mM dithioerythritol under argon. Thin-layer chromatography, chloroform:methanol, concentrated ammonia (10:10:3, v/v/v), was used to monitor the reaction.

After reduction was 50% complete, 15 minutes, the solution was slowly added with rapid stirring at room temperature to 200 μl of 5.3×10$^{-5}$M of (PDTP)$_6$-F(ab')$_2$ conjugate prepared in Example 2 under argon. The solution was stirred for 30 minutes after last addition and then applied to a 10×1 cm G-25 Sephadex column using 0.1M phosphate, 5 mM EDTA, pH 6.0 buffer to elute. The protein product, which eluted at the void volume of the column, was collected. Similarly, a second conjugate was prepared from 200 μl of 4.8×10$^{-5}$M of (PDTP)$_{12}$—F(ab')$_2$.

The number of conjugated fluoresceins per F(ab')$_2$ of the products was determined by UV-VIS spectroscopy at 492 nm and 280 nm in 0.5M sodium carbonate pH 9.5 buffer. The molar ratio of fluorescein to protein was calculated from the molar extinctions for bound fluorescein 76,800M$^{-1}$cm$^{-1}$ at 492 nm, 20,500M$^{-1}$cm$^{-1}$ at 280 nm, and from F(ab')$_2$ extinction of 1.48 $g^{-1}$1 cm$^{-1}$ at 280 nm and molecular weight of 92,000. The conjugates were found to have 1.9 and 5.7 fluoresceins per mole F(ab')$_2$, respectively, and were designated F'$_{1.9}$—F(ab')$_2$ and F'$_{5.7}$—F(ab')$_2$, respectively. (F' is F—NHCSNHCH$_2$CH$_2$SSCH$_2$CH$_2$CO—.)

In a similar manner, the (PDTP)$_n$ conjugates of ferritin, IgE, goat anti-IgE and T$_3$ were reacted with reduced DFDTH to obtain:

F'$_m$—ferritin;
F'$_m$—IgE;
F'$_m$—goat anti-IgE; and
F'—T$_3$, respectively.

EXAMPLE 4

Cleavage of Fluorescein from F'$_m$F(ab')$_2$ Conjugates with Dithioerythritol (DTE)

F'$_{1.9}$F(ab')$_2$ solution, 60 μl, was mixed with 20 μl of 1.5M tris pH 8.8 and 3 μl of 10 mM DTE in 0.1M phosphate, 5 mM EDTA, pH 6.0. Thin-layer chromatography, chloroform:methanol:concentrated ammonia (10:10:3, v/v/v) was used to monitor the reaction. After the cleavage reaction was greater than 90% complete, 30 minutes at room temperature, it was applied to a Sephadex G-25 column in a Pasteur Pipette (1.4 ml) using 0.1M phosphate, 5 mM EDTA, pH 6.0 buffer to elute. The protein fraction, which eluted at the void column of the column, was collected. The amount of remaining conjugated fluorescein was determined by UV-VIS spectroscoopy (described above). Cleavage of fluorescein from the protein was 94% complete. In an identical manner the extent of cleavage from the F'$_{5.7}$—F(ab')$_2$ was determined to be 98%.

EXAMPLE 5

Fluorescence Enhancement by Cleavage from Redissolved Immunocomplexes of F'$_m$F(ab')$_2$ Conjugates F'$_{1.9}$—F(ab')$_2$ conjugate (10 μl) and 10 μl goat anti-rabbit Ig (Western Chemical) were added to six assay tubes. Sodium phosphate, 0.01M—0.87% sodium chloride—0.1% sodium azide, pH 7.2 (10 μl, PBS) and 110 μl goat anti-rabbit Ig were added to six control tubes. After incubation for 15 minutes at room temperature, 800 μl of PBS was added to each tube. The tubes were centrifuged for 30 minutes at 3500 rpm. Supernatants were decanted and the pellets from three of the assay tubes and from three of the control tubes were dissolved by addition of 1.00 ml of 0.03M phosphate, 0.87% sodium chloride, 0.10% sodium azide, pH 11.9, buffer containing 2.46×10$^{-5}$M DTE.

Pellets of the remaining three assay tubes and three controls were dissolved in the same buffer without DET. All tubes were incubated for 1 hour at room temperature, then read on the Immpulse ™ Fluorometer (SCLAVO). The identical procedure was used for assaying $F'_{5.7}F(ab')_2$ conjugate. The results are summarized below as average relative fluorescence intensities (RFI).

| Sample | RFI (No DTE) | RFI (DTE) | Fluorescence enhancement ratio |
|---|---|---|---|
| $F'_{1.9}F(ab')_2$ | 37422 | 50134 | 1.34 |
| $F'_{5.7}F(ab')_2$ | 38720 | 67398 | 1.74 |

EXAMPLE 6

Determination of Ferritin in Serum

The conjugated labeled reagent synthesized in Example 3 using ferritin as specific reaction participant is used as a competitive reagent. Aliquots of serum can then be tested for ferritin by incubation at 37° C. for 4 hours with 20 μl containing the reagent in carbonate buffer, 0.01M, pH 8.6. To this is added 20 μl of goate anti-ferritin serum and followed by 20 μl of rabbit anti-goat Ig serum in phosphate-buffered saline. Following incubation to form the immune complex, 100 μl of cold 20% aqueous solution of polyethylene glycol (8,000 MW) is added to the mixture, and the resulting precipitate is separated by centrifugation. After discarding the supernatant, the precipitate is dissolved in aqueous phosphate buffer, pH 11.9.

The dissolved complex is treated with 25 μl of reducing agent containing 1.00 mM dithioerythritol. The resulting solution contains the dissociated 2-(5-fluoresceinylthioureido)ethyl mercaptan and is transferred to a flow cell for reading the fluorescence.

EXAMPLE 7

Determination of $T_3$

The $F'$ $T_3$ conjugate prepared in Example 3 is used as reagent. Samples are tested for the quantity of $T_3$ contained by treating the samples with goat anti-$T_3$ antibody attached to macrobeads to obtain an immune complex. After incubation at 37° C. for an hour, the beads are washed with phosphate buffered saline. The immune complex of the beads is then dissolved in base, and the dissolved complex treated with the dithioerythritol as above and the fluorescence measured.

EXAMPLE 8

Determination of IgE

Microtiter wells are coated with unlabeled goat anti-IgE antibody and treated with sample to be tested for IgE content. After washing, the wells are treated with reagent of Example 3 prepared with goat anti-IgE as the specific reaction participant. The wells are again washed and then treated with base to dissolve the complex. The complex is reacted with a solution containing $2.5 \times 10^{-5}$M dithioerythritol to release the fluorophore as the 2-(5-fluoresceinylthioureido)ethyl mercaptan.

EXAMPLE 9

Determination of $T_3$

The $F'$—$T_3$ prepared in Example 3 is used as reagent. Samples are tested for the quantity of $T_3$. The mixture of samples, $F'$—$T_3$ and goat anti-$T_3$ antibody solution is introduced to reaction vessel coated with anti-goat Ig antibody. After incubation, the vessels are washed, the immune complex is dissolved in base, and the dissolved complex treated with the dithioerythritol as above and the fluorescence measured.

We claim:

1. A method for determining the amount of an analyte in a sample suspected of containing the analyte, which method comprises:

reacting said sample with a reagent containing at least one substance specifically reactive with said analyte, obtaining an insoluble complex incorporating a cleavable detectable label, separating the complex from the liquid phase, redissolving said complex to obtain a solubilized complex, cleaving the detectable label from the solubilized complex, and detecting the cleaved label said label being conjugated to a component of said complex, through at least one bond cleavable under conditions compatible with said assay, wherein the cleavable bond permits the label to be released from the solubilized complex prior to measuring the amount of said label.

2. The method of claim 1 wherein the analyte is an antigen and immune complexing is conducted by mixing the sample with a known amount of antigen conjugated to label, said conjugate containing the cleavable bond, and reacting the mixture with an antibody, or and immunospecific fragment thereof, against said antigen.

3. The method of claim 2 which further comprises reacting the mixture with an antibody (or immunospecific portion thereof) specific against the anti-antigen antibody, or and immunospecific fragment thereof.

4. The method of claim 1 wherein the analyte component is an antigen and immune complexing is conducted by mixing the sample containing antigen with anti-antigen antibody, or an immunospecific fragment thereof, conjugated to label, said conjugate containing the cleavable bond.

5. The method of claim 1 wherein the the analyte is an antigen and immune complexing is conducted by mixing the sample with anti-antigen antibody and with labeled anti-antibody antibody, or an immunospecific fragment thereof, conjugated to label, said conjugate containing the cleavable bond.

6. The method of claim 1 wherein the analyte is an antibody, or an immunospecific fragment thereof, and immune complexing is conducted by mixing the sample with a known amount of said antibody or an immunospecific fragment thereof, conjugated to label, said conjugate containing the cleavable bond, and reacting the mixture with an antigen against said antibody, or an immunospecific fragment thereof.

7. The method of claim 6 which further comprises reacting the mixture with an additional antibody, or an immunospecific fragment thereof, specific against the antigen.

8. The method of claim 1 wherein the analyte component is an antibody, or an immunospecific fragment thereof, and immune complexing is conducted by mixing the sample containing antibody, or an immunospecific fragment thereof, with an antigen immunoreactive with said antibody, or an immunospecific fragment thereof, said antigen being conjugated to label, and said conjugate containing the cleavable bond.

9. The method of claim 1 wherein the analyte component is an antibody, or an immunospecific fragment thereof, and immune complexing is conducted by mixing the sample with an antigen immunoreactive with said antibody, or an immunospecific fragment thereof, and with a different antibody, or an immunospecific fragment thereof, reactive with the antigen, said different antibody, or an immunospecific fragment thereof being conjugated to label and said conjugate containing the cleavable bond.

10. The method of claim 1 wherein the separation of complex from the liquid phase is conducted by precipitation followed by separating the precipitate from the liquid phase.

11. The method of claim 1 wherein the analyte component is a substance specifically reactive with the analyte which is a non-Ig-related protein.

12. The method of claim 1 wherein the separation of complex from the liquid phase is conducted by attaching the complex to a solid support and removing the support from contact with the liquid phase.

13. The method of claim 10 wherein the separation of the precipitate from the liquid phase is effected by filtration.

14. The method of claim 10 wherein the separation of the precipitate from the liquid phase is effected by centrifugation.

* * * * *